(12) United States Patent
Crosby

(10) Patent No.: US 7,300,624 B2
(45) Date of Patent: Nov. 27, 2007

(54) METHOD OF DISINFECTING A BUILDING AIR SUPPLY

(76) Inventor: Bruce Kelly Krimpton Crosby, Unit 46-912 Lytton Street, North Vancouver, British Columbia (CA) V7H 2A5

( * ) Notice: Subject to any disclaimer, the term of this patent is extended or adjusted under 35 U.S.C. 154(b) by 344 days.

(21) Appl. No.: 10/967,253

(22) Filed: Oct. 19, 2004

(65) Prior Publication Data
US 2006/0083801 A1  Apr. 20, 2006

(51) Int. Cl.
*A61L 9/04* (2006.01)
(52) U.S. Cl. .......................................... 422/5; 422/124
(58) Field of Classification Search ...................... None
See application file for complete search history.

(56) References Cited

U.S. PATENT DOCUMENTS 3,795,438 A  *  3/1974  Westenholz et al. .......... 352/85
5,403,587 A      4/1995  McCue et al.
5,756,047 A  *  5/1998  West et al. .................... 422/37
2001/0034056 A1* 10/2001 Corey ........................ 435/266

FOREIGN PATENT DOCUMENTS

| CA | 2205070 | 11/1998 |
| JP | 2003181226 A | * 7/2003 |
| WO | WO 03019082 A1 | * 3/2003 |

* cited by examiner

Primary Examiner—E. Leigh McKane
(74) Attorney, Agent, or Firm—Clifford W. Vermette

(57) ABSTRACT

According to the invention there is provided a method of reducing microbial levels in the interior of a building, including vaporizing an anti-microbial essential oil to produce vaporized anti-microbial essential oil, entraining the vaporized anti-microbial essential oil in an air stream, and directing the air stream into the air ducts of the building and then into an interior air supply of the building.

7 Claims, 3 Drawing Sheets

METHOD OF DISINFECTING A BUILDING AIR SUPPLY

FIELD

The present invention relates to a method of disinfecting the air supply of a building.

BACKGROUND

The quality of the air supply of an inside of a building can often be contaminated with volatile organic compounds that are emissions from various sources that readily evaporate and mix with the air breathed by the occupants of the building. Volatile organic compounds are emitted from a variety of organic and inorganic materials including, for example: photocopiers, laser printers, dusts, cleaning fluid detergents, carpet emissions, furniture glues and paints, carpet glues, polishes and adhesives, scents from perfumes, ventilation system contaminants, fungi and moulds from damp areas, etc. Fungi spore fragments are ultra-fine particles of diameter less than 0.01 mm, which are easily and deeply ingested into the lungs. Such particles can cause damage to the lungs. They are one of the major concerns in a building because they are capable of multiplying and carry resistant pathogens, viruses and bacteria. Not only do fungi spores and spore fragments float in the air, but they collect on surfaces such as ceiling tiles where they can grow into a large biomass waiting for a triggering event to be released into the air.

Poor indoor air quality is responsible for a number of health problems, collectively known as Sick Building Syndrome. Such health problems include dryness and irritation of the eyes, nose and throat; difficulty concentrating on mental tasks; headache, fatigue and drowsiness; shortness of breath, itchy and dry skin; hypersensitivity and allergies. Illnesses from building related causes frequently affect the respiratory system. Flu-like symptoms such as fever, chills and shortness of breath, wheezing and fatigue frequently occur. In fact Legionnaires Disease is a building related disease caused by bacteria. Studies have shown that work productivity can rise by as much as 10% if the indoor air is clean and healthful.

Any substance used to treat building air must be safe for the occupants and at the same time have anti-microbial capabilities, which last a relatively long time. Essential oils are volatile oils distilled or extracted from plants such as thyme, lemongrass, citrus, anise, clove, aniseed, roses lavendar, citronella, cedar leaf, cinnamon leaf, camphor, etc. Such oils have been used for various medicinal purposes, as antiseptics and disinfectants, as insecticides, as food flavorings, and as solvents. Because of their hydrophobic nature essential oils cannot easily be formulated into aqueous mixtures. U.S. Pat. No. 5,403,587 issued to McCue et al. discloses that such oils can be solubilized or dispersed when combined in appropriate amounts with water and a solubilizing or dispersing agent and used for their anti-microbial properties. However, no studies have been done on the reduction in effectiveness of the essential oil caused by the carrier and surfactant or spreading agent.

SUMMARY OF THE INVENTION

According to the invention there is provided a method of reducing microbial levels in the interior of a building, which include vaporizing an anti-microbial essential oil to produce vaporized anti-microbial essential oil, entraining the vaporized anti-microbial essential oil in an air stream and directing the air stream into the air ducts of the building and then into an interior air supply of the building.

The air stream may be directed to a fresh air handler of a fresh air make-up system of the building for subsequent passage into the air ducts of the building and, ultimately, into the building interior.

The vaporizing step may include the following: placing balls made of chemical fibers in an air scrubber, coating surfaces of the balls with the anti-microbial essential oil and admitting fresh air into the air scrubber through the balls to vaporize the anti-microbial essential oil and directing the oil entrained in air after being vaporized out of an outlet of the air scrubber.

The concentration of anti-microbial essential oil may be varied by adjusting the rate of flow of air until a desired concentration of vaporized anti-microbial essential oil is inserted into the interior air supply of the building.

The anti-microbial essential oil is preferably cedar leaf oil.

The coating may be done by pumping the anti-microbial essential oil through a spiral wound perforated tube within the air scrubber and allowing the oil to drip onto and coat the surfaces of the balls.

BRIEF DESCRIPTION OF THE DRAWINGS

Further features and advantages will be apparent from the following detailed description, given by way of example, of a preferred embodiment taken in conjunction with the accompanying drawings, wherein.

DETAILED DESCRIPTION WITH REFERENCE TO THE DRAWINGS

Figures 1, 2:
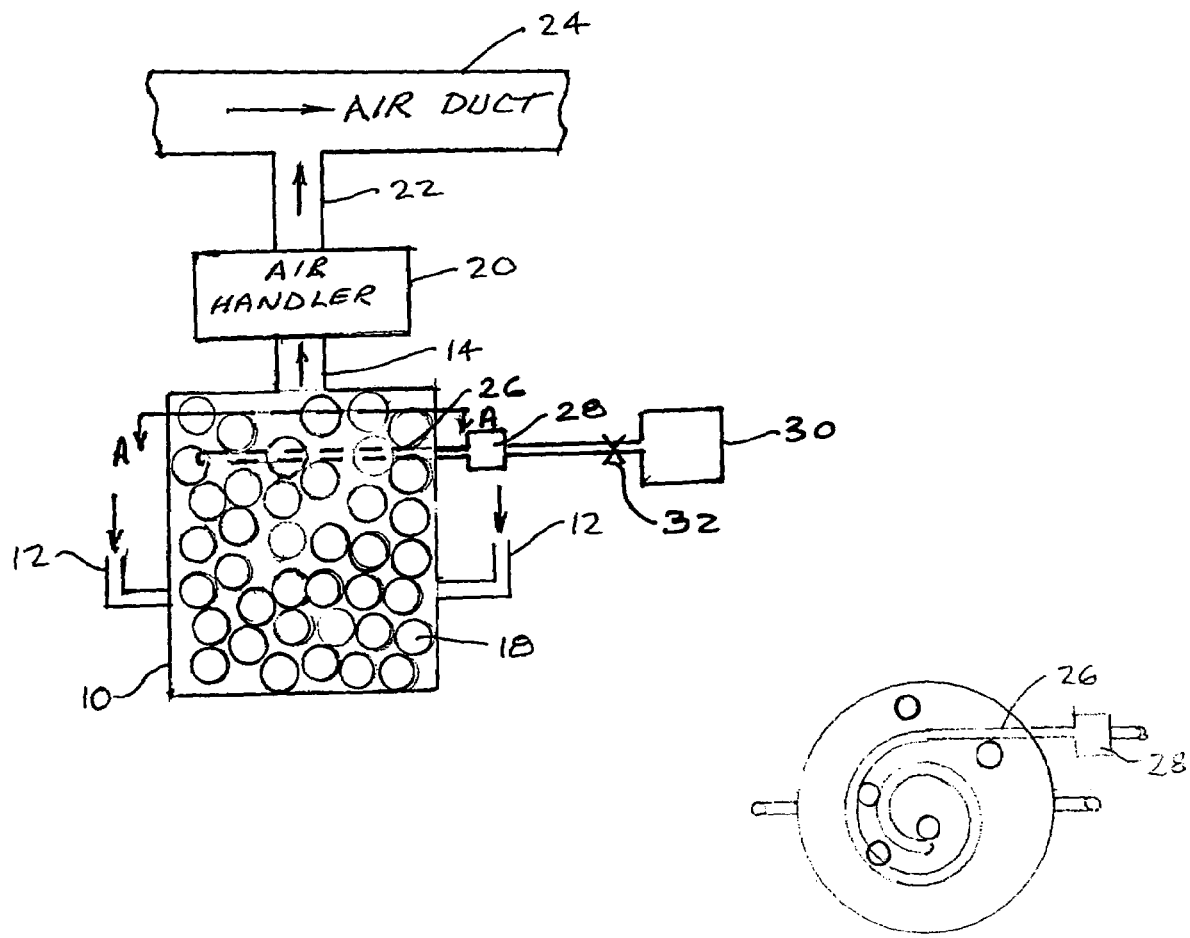
FIG. 1 is a schematic of the apparatus used to carry out the method herein.
FIG. 2 is a sectional view of the air scrubber and spiral wound tube used to coat the balls with cedar leaf oil.

In order to maximize the effectiveness of the essential oil, dispersion of the oil is made without the presence of a carrier such as water or any other substance. In order to accomplish this an ordinary air scrubber 10, shown in FIGS. 1 and 2, was filled 1 inch plastic balls 18 known as "bio balls" (trademark). Inlets 12 at diametrically opposite sides of the cylindrical surface of the scrubber 10 admit fresh air while the outlet 14 is coupled to a fresh air handler 20 of a building air make-up system. The fresh air handler 20 couples by duct 22 to an air duct 24 of a building. A helically wound, perforated tube 26 winds through the balls 18 and couples to a small pump 28 exterior of the air scrubber 10 and through a valve 32 to a reservoir of cedar leaf oil 30.

Activation of pump 28 causes cedar leaf oil under pressure to flow into the spiral tube 26 and drip out of the perforations in the tube to coat the balls 18. At the same time fresh air is drawn into inlets 12. The incoming air causes movement of the plastic balls and results in vaporizing the cedar leaf oil coating their surfaces and its entrainment in the air stream leading to the fresh air handler 20. The fresh air handler 20 then distributes the cedar leaf oil vapour into the building ducts 24 and then into the interior of the building where it kills organisms in both the air and on surfaces that produce harmful volatile organic compounds.

Figure 3:
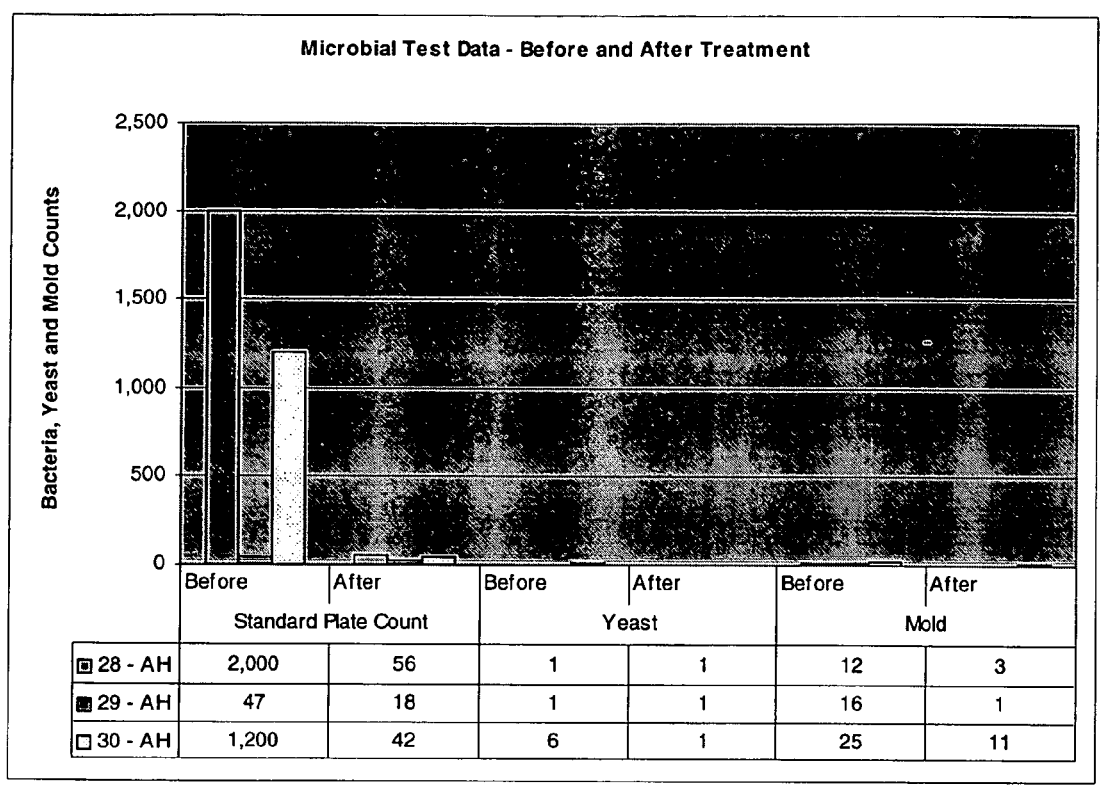
FIG. 3 is graph showing the bacterial, yeast and mold counts from the interior of a test building before and after treatment with cedar leaf oil.

In a test of the system on a large (33 story) AAA rated building, swabs were first taken on the floors which exhibited the highest microbial counts to determine the plate count of all bacterial organisms present before the treatment. The system was then activated during evenings and weekends for four consecutive weeks. After this time, a second set of swab tests were taken. FIG. 3 shows the dramatic improvement in the standard plate count or count of all bacterial organisms present.

Figure 4:
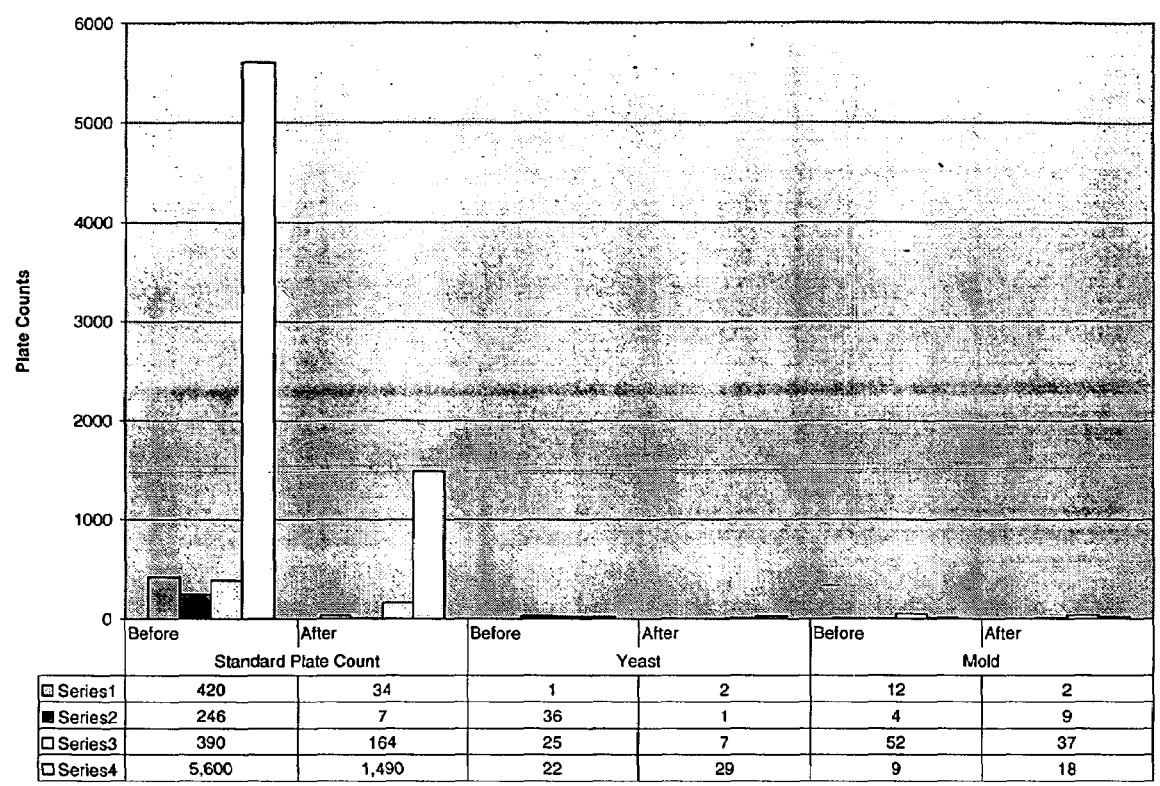
FIG. 4 is a graph as in FIG. 2 taken for a different set of floors.

In a second test swabs were taken from a different set of floors identified as having high plate counts. The cedar leaf oil diffusion system was activated during weekdays from 9:00 am to 5:00 pm and deactivated during weekends. Tests taken after 1 month showed the results indicted in FIG. 4.

Accordingly, while this invention has been described with reference to illustrative embodiments, this description is not intended to be construed in a limiting sense. Various modifications of the illustrative embodiments, as well as other embodiments of the invention, will be apparent to persons skilled in the art upon reference to this description. It is therefore contemplated that the appended claims will cover any such modifications or embodiments as fall within the true scope of the invention.

I claim:

1. A method of reducing microbial levels in the interior of a building, comprising:
   (a) vaporizing an anti-microbial essential oil to produce vaporized anti-microbial essential oil, the vaporizing comprising the steps of:
      i. placing balls made of chemical fibers in an air scrubber;
      ii. coating the surfaces of the balls with the anti-microbial essential oil by:
         a. placing a spiral wound tube within the air scrubber, the tube having perforations therein, and,
         b. pumping the essential oil through the tube so that the essential oil escapes through the perforations and coats the surfaces of the balls; and,
      iii. admitting a stream of air into the air scrubber through the balls to vaporize the anti-microbial essential oil and entrain the vaporized oil in the air stream;
   (b) directing the resulting oil-entrained air stream out of an outlet of the air scrubber; and,
   (c) directing the air stream of step (b) into the air ducts of the building and thereby into an interior air supply of the building.

2. In a building of the type having at least one air duct carrying an air stream into the building's interior, a method of entraining the air stream with a vaporized essential oil, said method comprising the steps of:
   (a) placing balls in an air scrubber that is in communication with the air duct;
   (b) coating the surface of the balls of step (a) with at least one essential oil by
      i. providing a perforated spiral wound or helical tube within the air scrubber such that essential oil pumped through the perforated spiral wound or helical tube exits the perforated spiral wound or helical tube through the perforations and drips onto the balls; and,
      ii. pumping the essential oil through the perforated spiral wound or helical tube, thereby coating the surface of the balls with the essential oil;
   (c) directing the air stream into the air scrubber and though the balls, thereby vaporizing the essential oil coating the surface of the balls and entraining the air stream with the vaporized essential oil; and,
   (d) directing the air stream out of the air scrubber and into the air duct.

3. The method of claim 2 wherein at least one of the essential oils of step (b) is an anti-microbial essential oil.

4. The method of claim 2 wherein at least one of the essential oils of step (b) is cedar leaf oil.

5. The method of claim 2 further comprising the step of adjusting the rate of flow of the air stream of step (c) in order to obtain a desired concentration of the essential oil entrained in the air stream.

6. The method of claim 2 wherein the balls placed in step (a) are made of chemical fibers.

7. The method of claim 2 wherein the perforated spiral wound or helical tube provided in step (b) winds through the balls of step (a).

* * * * *